US007973128B2

United States Patent
Kosmatopoulos et al.

(10) Patent No.: US 7,973,128 B2
(45) Date of Patent: Jul. 5, 2011

(54) IMMUNOGENIC POLYPEPTIDE COMPOSED OF TUMOR ANTIGEN-DERIVED OPTIMIZED CRYPTIC PEPTIDES, AND USES THEREOF

(75) Inventors: Kostantinos Kosmatopoulos, Paris (FR); Sébastien Cornet, Lille (FR)

(73) Assignee: Vaxon Biotech, Evry Cedex (FR)

(*) Notice: Subject to any disclaimer, the term of this patent is extended or adjusted under 35 U.S.C. 154(b) by 281 days.

(21) Appl. No.: 12/158,736

(22) PCT Filed: Dec. 23, 2005

(86) PCT No.: PCT/EP2005/014212
§ 371 (c)(1),
(2), (4) Date: Oct. 16, 2008

(87) PCT Pub. No.: WO2007/073768
PCT Pub. Date: Jul. 5, 2007

(65) Prior Publication Data
US 2009/0130133 A1    May 21, 2009

(51) Int. Cl.
*A61K 38/00* (2006.01)
*C07K 14/00* (2006.01)
*A61P 35/00* (2006.01)
*C07H 21/02* (2006.01)
*C07H 21/04* (2006.01)
*C12N 15/00* (2006.01)
*C12N 5/00* (2006.01)
*C12N 5/07* (2010.01)

(52) U.S. Cl. ........ 530/300; 530/324; 514/1.1; 514/19.2; 514/19.3; 514/19.4; 536/23.1; 536/23.4; 435/320.1; 435/325; 435/355

(58) Field of Classification Search .................. None
See application file for complete search history.

(56) References Cited

U.S. PATENT DOCUMENTS
2004/0072240 A1* 4/2004 Kosmatopoulos et al. .... 435/7.1

FOREIGN PATENT DOCUMENTS
EP    1 568 373 A    8/2005
WO    WO 01/85932    11/2001

OTHER PUBLICATIONS

Suhrbier A. (Expert Rev. Vaccines 2002 1:207-213).*
Velders et al. (J. Immunol. 2001 166:5366-5373).*
Thomson et al. (J. Virol. 1998 72:2246-2252).*
Wang et al. (J. Immunol. 1998 161-5516-5524).*
Search Report and Written Opinion for International Application No. PCT/EP2005/014212, filed Dec. 23, 2005.
Mateo L et al: "An HLA-A2 polyepitope vaccine for melanoma immunotherapy"; Journal of Immunology, The Williams and Wilkins Co. Baltimore, US; vol. 163, No. 7; Oct. 1, 1999; pp. 4058-4063; XP002244411.
Scardino A et al: "Her-2/Neu and HTERT Cryptic Epitopes as Novel Targets for Broad Spectrum Tumor Immunotherapy"; Journal of Immunology, The Williams and Wilkins Co. Baltimore, US; vol. 168, No. 11; Jun. 1, 2000; pp. 5900-5906; XP001126974.
Graff-Dubois S et al: "Generation of CTL Recognizing an HLA-A 0201 Restricted Epitope Shared by MAGE-A1, -A2, -A3, -A4, -A6, -A10, and -A12 Tumor Antigens: Implication in a Broad-Spectrum Tumor Immunotherapy"; Journal of Immunology, The Williams and Wilkins Co. Baltimore, US; vol. 169, No. 1, 2002; pp. 575-580; XP001109368.
Alexander Jeff et al: "A decaepitope polypeptide primes for multiple CD8+ IFN-gamma and Th lymphocyte responses: Evaluation of multiepitope polypeptides as a mode for vaccine delivery"; Journal of Immunology; vol. 168, No. 12; Jun. 15, 2002; pp. 6189-6198; XP002372921.
Cornet Sebastien et al: "Optimal organization of a polypeptide-based candidate cancer vaccine composed of cryptic tumor peptides with enhanced immunogenicity"; Vaccine; Mar. 15, 2006; vol. 24, No. 12; pp. 2102-2109; XP002372922.

* cited by examiner

*Primary Examiner* — Peter J Reddig
(74) *Attorney, Agent, or Firm* — Alston & Bird LLP

(57) ABSTRACT

The present invention pertains to the field of anti-cancer vaccines. More particularly, the invention concerns an optimized polypeptide, which comprises three cryptic tumor peptides with enhanced immunogenicity and comprises the amino acids sequence YLQVNSLQTVYLEYRQVPVYLEEIT-GYL (SEQ ID NO: 2), for use in an anti-cancer vaccine. Nucleic acids encoding such a polypeptide, as well as complexes and dendritic cells engineered with this polypeptide or a nucleic acid encoding it, are also part of the invention.

21 Claims, 1 Drawing Sheet

Figure 1:
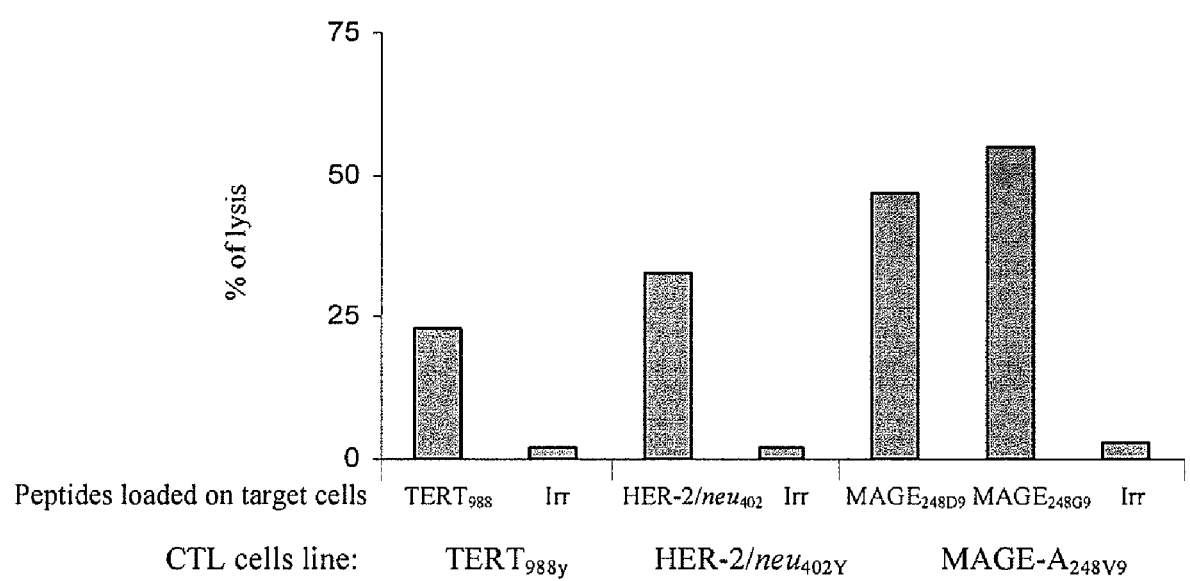

IMMUNOGENIC POLYPEPTIDE COMPOSED OF TUMOR ANTIGEN-DERIVED OPTIMIZED CRYPTIC PEPTIDES, AND USES THEREOF

CROSS REFERENCE TO RELATED APPLICATIONS

This application is a national stage application filed under 35 U.S.C. 371 of International Application No. PCT/EP2005/014212, filed Dec. 23, 2005.

FIELD AND BACKGROUND OF THE INVENTION

The present invention pertains to the field of anti-cancer vaccines. More particularly, the invention relates to an optimized polypeptide for use in an anti-cancer vaccine, which comprises three cryptic tumor peptides with enhanced immunogenicity.

The recent identification of tumor-associated antigens targeted by antitumor cytotoxic T lymphocytes (CTL) has opened the way to cancer vaccine approaches aimed at stimulating the tumor-specific CTL repertoire.

Experimental antitumor vaccines take many forms, including free peptides, dendritic cells loaded with peptides or tumor lysates, and DNA. Although peptide based vaccines are very attractive over other forms in term of feasibility, many studies, with dominant tumor peptides were found to elicit only weak immunological and clinical responses, with strong inter-patient variability (Rosenberg et al., 2004). Several factors may explain these relatively disappointing results. First, most tumor antigens are non-mutated self proteins also expressed by normal tissues, including the thymus. This raises issues of tolerance of the tumor-specific CTL repertoire (Restifo, 2001; Van Pel et al., 1995), which involves dominant rather than cryptic peptides (Cibotti et al., 1992; Nanda and Sercarz, 1995; Restifo, 2001). In fact, it was recently demonstrated that cryptic peptides induced antitumor immunity more efficiently than dominant peptides (Gross et al., 2004).

Second, approaches based on single epitopes induce an HLA-restricted CTL response against only one antigen which, owing to the genetic instability of tumors, may be not expressed by all tumor cells (Brasseur et al., 1995; Lehmann et al., 1995). Approaches eliciting CTL responses to multiple antigens would have several potential advantages. In particular, expression of at least one target antigen should be sufficient to trigger cytotoxicity, and tumor cells are unlikely to lose all the target antigens simultaneously, especially when the antigens in question are essential for cell survival and tumor growth. This approach can elicit strong immune responses (Oukka et al., 1996).

Finally, broad-spectrum cancer immunotherapy should target universal tumor antigens, such as TERT, HER-2/neu, MUC-1 and MAGE-A, that are over-expressed by a wide variety of tumors (Minev et al., 2000; Ofuji et al., 1998; Ogata et al., 1992; Reese and Slamon, 1997; Slamon et al., 1987; Van den Eynde and van der Bruggen, 1997; Vonderheide et al., 1999). Most of these antigens are involved in tumor cell survival and tumorigenicity, and their down-regulation to escape the immune response may therefore have deleterious effect on tumor growth.

In order to respond to at least part of the issues mentioned above, the inventors have combined three universal tumor-antigen-derived optimized cryptic peptides ($TERT_{988Y}$, $HER-2/neu_{402Y}$ and $MAGE-A_{248V9}$) in several 28-amino acid polypeptides, and evaluated the capacity of the obtained polypeptides to induce an immune response against all three peptides simultaneously, both in vivo in HLA-A*0201 transgenic (HHD) mice and in vitro in healthy human donor. Each of the three peptides had previously been shown to elicit an antitumor response in vivo and in vitro (Gross et al., 2004; Scardino et al., 2002). Interestingly, CTL elicited by $MAGE-A_{248V9}$ targeted all MAGE-A antigens (-A1, -A2, -A3, -A4, -A6, -A10, -A12) (Graff-Dubois et al., 2002).

As described below, the inventors demonstrated that a) a polypeptide consisting of $TERT_{988Y}$, $HER-2/neu_{402Y}$ and $MAGE-A_{248V9}$ elicits a polyspecific CTL response, contrary to a simple mixture of the three peptides; b) the capacity of the polypeptide to induce a polyspecific CTL response depends on its internal organization: among the six variants corresponding to all possible arrangements of the three peptides, only one produced a trispecific CTL response in almost all experiments with mice and human cells.

SUMMARY OF THE INVENTION

A first aspect of the invention is hence a polypeptide which comprises the sequence YLQVNSLQTVX$_1$X$_2$X$_3$YLEYRQVPVX$_1$X$_2$X$_3$YLEEITGYL (SEQ ID No: 1). In this sequence, the $TERT_{988Y}$, $MAGE-A_{248V9}$ and $HER-2/neu_{402Y}$ epitopes are separated by spacers X$_1$X$_2$X$_3$, in which X$_1$, X$_2$ and X$_3$ are any amino acid or none. The polypeptide is hence at least 28-aminoacids long; its length can be increased by the addition of spacers between the epitopes, and/or by the addition of signals, at its N-terminal and/or C-terminal extremities, which favor its processing. In particular, the polypeptide according to the invention can further comprise an endoplasmic reticulum-translocating signal sequence at its N-terminal extremity. Several endoplasmic reticulum-translocating signal sequences have been described in the scientific literature and cane be used in the context of the invention. For example, the Ig kappa-chain signal sequence (Ishioka et al., 1999), and the E3/19-kD protein signal sequence (Anderson et al., 1991) can be added at the N-terminal extremity of the peptides according to the invention. Alternatively or in addition, the polypeptide according to the invention can further comprise ubiquitin at its C-terminal extremity, since ubiquitination of proteins results in increased proteolysis.

In a preferred embodiment of the polypeptide according to the invention, X$_1$=X$_2$=X$_3$=none. This means that the three epitopes are directly bound to each other. In the absence of ubiquitin and ER-translocating signal, the polypeptide is hence the Poly-6 polypeptide illustrated in the examples below, the sequence of which is YLQVNSLQTVYLEYRQVPVYLEEITGYL (SEQ ID No: 2).

According to another embodiment, the spacers between the epitopes are AAY, which means that X$_1$=X$_2$=A and X$_3$=Y.

In the polypeptides according to the invention, the amino acids can be either L- or D-amino acids.

A polypeptide according to the invention preferably exhibits one or both of the following properties, which are indicative of good immunogenicity:

it induces a trispecific CD8+ T cells response against $TERT_{988Y}$, $MAGE-A_{248V9}$, and $HER-2/neu_{402Y}$ in a majority of HHD mice vaccinated with said polypeptide;

it induces a trispecific CD8+ T cells response against $TERT_{988Y}$, $MAGE-A_{248V9}$, and $HER-2/neu_{402Y}$ in an in vitro assay with human PBMC from healthy HLA-A*0201 donors; this trispecific response is preferably obtained with PBMC from a majority, more preferably at least 70%, of healthy HLA-A*0201 donors.

These properties can easily be tested by the skilled artisan, using the protocols and assays described in the experimental part below.

Another object of the present invention is a nucleic acid molecule encoding a polypeptide as described above. In a preferred embodiment, the nucleic acid molecule is an expression vector. By "expression vector" is meant a molecule which, when introduced in a mammalian cell, enables the expression of said encoded polypeptide. To that aim, the skilled artisan can choose an appropriate transcription promoter (for example, the CMV promoter), a coding sequence with codons optimized for expression in human cells, an appropriate translation termination sequence, optionally a Kozak consensus sequence, etc. The nucleic acid molecule is preferably a DNA molecule.

A third aspect of the invention is an isolated dendritic cell loaded with a polypeptide as above-described, or transduced with a nucleic acid molecule encoding such a polypeptide. In the present context "isolated" means that said dendritic cell is outside the body of the patient. The cell is preferably loaded or transduced ex vivo. For example, the dendritic cell can be loaded with the polypeptide by the technique described by Vonderheide et al. (Vonderheide et al., 2004), or transduced with an expression vector using the protocol described by Firat et al. (Firat et al., 2002).

The invention also pertains to a complex comprising a peptide delivery vector and a polypeptide as described above. Examples of peptide delivery vectors that can be used according to the invention are cell-penetrating peptides, bacterial toxins such as the adenylate cyclase of *B. pertussis* (Fayolle et al., 1999), the diphtheria toxin (Fayolle et al., 1999), the anthrax toxin (Doling et al., 1999), the B subunit of shiga toxin (Haicheur et al., 2000) and other vectors such as the bee venom PLA2 (Babon et al., 2005), liposomes, virosomes (Bungener et al., 2002) and the like.

Another kind of complex according to the invention comprises a gene delivery vector and a nucleic acid molecule as above-described. A huge variety of gene delivery vectors have been described to date, among which the skilled artisan can make a choice depending on the way of administration which is contemplated (ex vivo, intra-tumoral, systemic, . . . ), the type of target cells, etc. Non-limitative examples of gene delivery vectors which can be used according to the invention are non viral vectors such as liposomes, cell-penetrating peptides, nanoparticles (like gold particles for gene gun administration), bacteria (Vassaux et al., 2005) and viral vectors such as MVA (Meseda et al., 2005), adenovirus, adeno-associated virus, retrovirus, lentivirus and the like, which are abundantly described in the scientific literature.

The invention also concerns a pharmaceutical composition comprising a polypeptide and/or a nucleic acid molecule and/or a complex and/or engineered dendritic cells as described above. In particular, polypeptides, nucleic acid molecules, complexes and dendritic cells according to the invention can be used for the preparation of an immunogenic composition for anti-cancer immunotherapy. These compositions are particularly useful for immunotherapy of tumors which express at least one antigen selected in the group consisting of the MAGE-A family, the HER family and TERT, especially for treating HLA-A*0201 individuals.

Cancer vaccination or treatment methods, comprising a step of administrating a polypeptide and/or a nucleic acid molecule and/or a complex according to the invention, either in vivo to a patient in need thereof, or ex vivo to cells originating from said patient, are also part of the invention, as well as vaccination or treatment methods comprising a step of administrating engineered dendritic cells as described above to an individual.

The invention is further illustrated by the following FIGURE and examples.

FIGURE LEGEND

FIG. 1: Recognition of cognate native peptides by mouse CTL induced by optimized cryptic peptides.

CTL lines were derived from splenocytes of HHD mice immunized against optimized cryptic peptides, as described in Materials and Methods. CTL lines were tested for cytotoxicity against RMAS/HHD targets loaded with an irrelevant peptide (HIVgag76) or with the cognate native peptide, at a lymphocyte to target cell ratio of 10/1.

EXAMPLES

Example 1

Materials and Methods 1.1. Animals

HLA-A*0201 transgenic HHD mice have been described elsewhere (Pascolo et al., 1997).

1.2. Cells

Murine RMAS/HHD cells have been described elsewhere (Pascolo et al., 1997). HLA-A*0201-expressing human tumor T2 cells are TAP1/2-deficient. All cells were grown in RPMI 1640 or DMEM medium supplemented with 10% fetal calf serum (FCS).

1.3. Peptides

The peptides were synthesized by Epytop (Nîmes, France)

1.4. Measurement of Peptide/HLA-A*0201 Relative Affinity and Stability

The protocol used to measure relative affinity (RA) is described in detail elsewhere (Tourdot et al., 2000). Briefly, T2 cells were incubated with various peptide concentrations (0.1-100 μM) for 16 h and were then labeled with mAb BB7.2 to quantify HLA-A*0201 expression. At each peptide concentration, HLA-A*0201-specific labeling was calculated as a percentage of the labeling obtained with the reference peptide HIVpol$_{589}$ (IVGAETFYV) used at 100 μM. Relative affinity was calculated as the test peptide concentration divided by the reference peptide concentration that induced 20% HLA-A*0201 expression. To measure peptide/HLA-A*0201 complex stability, T2 cells were incubated overnight with each peptide at 100 μM and 37° C. The cells were then treated with Brefeldin A for 1 h, washed, incubated at 37° C. for 0, 2, 4 and 6 hours, and labeled with mAb BB7.2. DC$_{50}$ was defined as the time required for 50% loss of HLA-A*0201, as previously described (Tourdot et al., 2000).

1.5. Generation of CTL in HHD Mice

HHD mice were injected subcutaneously with 100 μg of nonamer/decamer peptides, and with 240 μg of polypeptide emulsified in incomplete Freund's adjuvant (IFA) plus 150 μg of the I-A$^b$ restricted HBVcore$_{128}$ T-helper epitope. Eleven days later spleen cells (5×10$^7$ cells in 10 ml) from immunized mice were stimulated in vitro with peptide (10 μM) in RPMI 1640+10% FCS for five days. The CTL lines were established by weekly re-stimulation in vitro with irradiated spleen cells in the presence of diminishing peptide concentrations (1 to 0.1 μM) and 50 U/ml IL-2 (Proleukin, Chiron Corp., Emeryville, Calif.).

1.6. Cytotoxicity Assay

Murine RMAS/HHD cells were used as targets, as described elsewhere (Tourdot et al., 1997). Briefly, 2.5×10³ ₅₁Cr-labeled targets were pulsed with peptides at 37° C. for 60 min. Effector cells in 100 µl of medium were then added and incubated at 37° C. for 4 hours. After incubation, 100 µl of supernatant was collected and radioactivity was measured in a γ-counter. The percentage of specific lysis was determined as: Lysis=(Experimental Release–Spontaneous Release)/(Maximal Release–Spontaneous Release)×100.

1.7. Flow Cytometric Immunofluorescence Analysis

For tetramer labeling, cells from inguinal and para-aortic lymph nodes (LN) of immunized mice were stained with 15 µg/ml PE-coupled HLA-A2/TERT$_{988Y}$, HLA-A2/MAGE-A$_{248V9}$ and HLA-A2/HER-2/neu$_{402Y}$ tetramers (Proimmune, Oxford, UK) in the presence of an anti-Fc receptor antibody (clone 2.4 G2) in 20 µl of PBS, 2% FCS for 1 h at room temperature. The cells were washed once in PBS, 2% FCS and then stained with anti-CD44-FITC (clone 1M.178), anti-TCRβ-cychrome (clone H57) and anti-CD8α-APC (clone 53.6.7) (BD Biosciences, Le Pont de Claix, France) in 50 µl of PBS, 2% FCS for 30 min at 4° C. The cells were then washed once in PBS, 2% FCS and immediately analyzed in a FACSCalibur® flow cytometer (Becton Dickinson, San Jose, Calif., USA).

1.8. Generation of CD8 Cells from Human Peripheral Blood Mononuclear Cells (PBMC)

PBMC were collected by leukapheresis from healthy HLA-A*0201 volunteers. Dendritic cells (DC) were produced from adherent cells (2×10⁶ cells/ml) cultured for seven days with 500 IU/ml GM-CSF (Leucomax®, Schering-Plough, Kenilworth, N.J.) and 500 IU/ml IL-4 (R&D Systems, Minneapolis, Minn.) in complete medium (RPMI 1640 supplemented with 10% heat-inactivated human AB serum, 2 µM L-glutamine and antibiotics). On day 7, DC were pulsed with 10 µM peptides or polypeptides for 2 h; the maturation agents Poly I:C (Sigma, Oakville, Canada) at 100 ng/ml, and anti-CD40 mAb (clone G28-5, ATCC, Manassas, Va.) at 2 µg/ml were added to the culture and DCs were further incubated at 37° C. overnight or for up to 48 hours. Mature DC were then irradiated (3500 rads). CD8+ cells were purified by positive selection with CD8 MicroBeads (Miltenyi Biotec, Auburn, Calif.) according to the manufacturer's instructions. CD8⁺ cells (2×10⁵)+CD8⁻ cells (6×10⁴) were stimulated with 2×10⁴ peptide-pulsed DC in complete culture medium supplemented with 1000 IU/ml IL-6 and 5 IU/ml IL-12 (R&D Systems, Minneapolis, Minn.) in round-bottomed 96-well plates. From day 7, cultures were restimulated weekly with peptide-loaded DC in the presence of 20 IU/ml IL-2 (Proleukin, Chiron Corp., Emeryville, Calif.) and 10 ng/ml IL-7 (R&D Systems, Minneapolis, Minn.). After the third restimulation, CD8 cells were tested in an IFN-γ release assay.

1.9. Intracellular IFN-γ Labeling

T cells (10⁵) were incubated with 2×10⁵ T2 cells loaded with stimulating peptide in the presence of 20 µg/ml Brefeldin-A (Sigma, Oakville, Canada). Six hours later they were washed, stained with r-phycoerythrin-conjugated anti-CD8 antibody (Caltag Laboratories, Burlingame, Calif.) in PBS for 25 min at 4° C., washed again, and fixed with 4% PFA. The cells were then permeabilized with PBS, 0.5% BSA, 0.2% saponin (Sigma, Oakville, Canada), and labeled with an allophycocyanin-conjugated anti-IFNγ mAb (PharMingen, Mississauga, Canada) for 25 min at 4° C. before analysis with a FACSCalibur™ flow cytometer (Becton Dickinson, Mountain View, Calif.).

Example 2

Immunogenicity of the Peptides Used to Generate the Polypeptide

Three peptides were selected to be included in the polypeptide. HER-2/neu$_{402Y}$ and TERT$_{988Y}$ are the optimized variants of the low-HLA-A*0201-affinity cryptic peptides HER-2/neu$_{402}$ and TERT$_{988}$, themselves derived from the widely expressed tumor antigens HER-2/neu and TERT (Scardino et al., 2002). They differ from the native peptides at position 1, where the native residue is replaced by a Y. This substitution enhances the affinity of HLA-A*0201-restricted cryptic peptides (Tourdot et al., 2000). MAGE-A$_{248V9}$ is the optimized variant of the low-HLA-A*0201-affinity MAGE-A$_{248D9/G9}$ that is common to all MAGE-A molecules. It differs from the native peptides at position 9, where the amino acids D/G are replaced by the primary anchor residue V. This substitution also enhances HLA-A*0201 affinity (Graff-Dubois et al., 2002).

All three peptides exhibited high HLA-A*0201 binding affinity (RA<5) and formed stable HLA/peptide complexes (DC50>2 h) (Graff-Dubois et al., 2002; Scardino et al., 2002) (Table 1). As previously shown, all three peptides were immunogenic in HLA-A*0201 transgenic HHD mice (Graff-Dubois et al., 2002; Scardino et al., 2002). More importantly, mouse CTL lines specifically recognized and killed RMAS/HHD targets loaded with the appropriate native peptide (FIG. 1).

TABLE 1

HLA-A*0201 affinity of the peptides MAGE-A$_{248V9}$, HER-2/neu$_{402Y}$ and TERT$_{988Y}$.

| Peptide | Sequence | RA[1] | DC$_{50}$[2] |
|---|---|---|---|
| TERT$_{988Y}$ | LQVNSLQTV (SEQ ID No: 8) | 2.1 | >6 |
| HER-2/neu$_{402Y}$ | YLEEITGYL (SEQ ID No: 10) | 3.6 | 4 |
| MAGE-A$_{248V9}$ | YLEYRQVPV (SEQ ID No: 9) | 1.8 | 4 |

[1]RA = Relative Affinity; concentration of experimental peptide/concentration of reference peptide that induced 20% of HLA-A*0201 expression obtained with 100 µM reference peptide. Affinity of the reference peptide = 1.
[2]DC50: Dissociation complex 50: half-life of the HLA/peptide complex (h)

Example 3

Immune Responses to the Peptide Mixture

The simplest way to stimulate a polyspecific CTL response in vivo would be to inject a mixture of the relevant peptides. Therefore, the inventors examined whether HHD mice vaccinated with an equimolar mixture of peptides HER-2/neu$_{402Y}$, TERT$_{988Y}$ and MAGE-A$_{248V9}$ developed a polyspecific response in vivo. The immune response was evaluated by measuring the frequency of peptide-specific CD8 T cells in the lymph nodes draining the injection site seven days after vaccination, using specific tetramers. Before use, each tetramer was validated with peptide-specific CTL lines as previously described (Miconnet et al., 2002). A positive response was recorded when the percentage of tetramer-positive CD8 cells was higher than the mean percentage+3 standard deviations of tetramer-positive CD8 cells in six naive mice (0.16% for MAGE-A$_{248V9}$, 0.13% for HER-2/neu$_{402Y}$ and 0.16% for TERT$_{988Y}$). Eight mice were vaccinated with the peptide mixture in two independent experiments (Table 2). None of the eight mice responded simultaneously to all three peptides. Three mice responded to one peptide and five responded to two peptides. Responses to MAGE-A$_{248V9}$ were more frequent (6/8 mice) than responses to HER-2/neu$_{402Y}$ (4/8 mice) or TERT$_{988Y}$ (3/8 mice).

TABLE 2

CD8 T cell responses against MAGE-A$_{248V9}$, HER-2/neu$_{402Y}$ and TERT$_{988Y}$ in individual mice immunized with an equimolar peptide mixture.

| Mouse | Specific T CD8 response against | | |
|---|---|---|---|
| | MAGE-A$_{248V9}$ | HER-2/neu$_{402Y}$ | TERT$_{988Y}$ |
| #1 | ++ | − | − |
| #2 | + | + | − |
| #3 | + | − | − |
| #4 | + | − | − |
| #5 | − | ++ | + |
| #6 | − | ++ | ++ |
| #7 | + | − | ++ |
| #8 | + | ++ | − |

"+": the percentage of tetramer-positive CD8 T cells was between one and two-fold the cutoff, as defined in Materials and Methods (0.16% for MAGE-A$_{248V9}$, 0.13% for HER-2/neu$_{402Y}$, and 0.16% for TERT$_{988Y}$).
"++": the percentage of tetramer-positive CD8 T cells was more than twice the cutoff.

The inability of the peptide mixture to stimulate a trispecific CD8 T cell response was confirmed in vitro with human cells. PBMC from three HLA-A*0201 donors were stimulated in vitro with a mixture of MAGE-A$_{248V9}$, HER-2/neU$_{402Y}$ and TERT$_{988Y}$ and, after four cycles of restimulation, were tested for their capacity to recognize and be activated by stimulator cells loaded with each peptide. PBMC activation was evaluated by measuring the percentage of IFNγ-producing CD8 cells by means of intracellular labeling. A positive response was recorded when the percentage of activated PBMC was at least twice that obtained with an irrelevant peptide. None of the three donors developed a specific CD8 T cell response against all three peptides (Table 3). Donor #D5725 responded to MAGE-A$_{248V9}$/HER-2/neu$_{402Y}$, donor #D7241 responded to HER-2/neU$_{402Y}$, and donor #D7225 responded to MAGE-A$_{248V9}$/TERT$_{988Y}$.

TABLE 3

Peptide-specific CD8 T cells induced by stimulation of healthy donor PBMC with the peptide mixture. Peptide-specific CD8 T cells were generated by in vitro stimulation of PBMC from three healthy donors with an equimolar mixture of MAGE-A$_{248V9}$, HER-2/neu$_{402Y}$ and TERT$_{988Y}$ peptides. The specificity of induced CD8 T cells was evaluated by measuring the % of IFNγ-producing CD8 cells after stimulation with peptide-loaded T2 cells as described in Materials and Methods.
Values more than twice the negative control value, indicating a positive response, are shown in bold.

| PBMC donor | % of IFNγ-producing CD8 cells in response to | | | |
|---|---|---|---|---|
| | MAGE-A$_{248V9}$ | HER-2/neu$_{402Y}$ | TERT$_{988Y}$ | Irrelevant |
| D5725 | 0.29 | 0.33 | 0.09 | 0.09 |
| D7225 | 0.32 | 0.54 | 0.24 | 0.27 |
| D7241 | 2.84 | 0.36 | 1.21 | 0.22 |

These results demonstrated that vaccination with a simple mixture of immunogenic peptides did not generate a polyspecific response.

Example 4

Polypeptide Immunogenicity

The inventors then examined whether vaccination with polypeptides composed of MAGE-A$_{248V9}$, HER-2/neu$_{402Y}$ and TERT$_{988Y}$ elicited a trispecific CD8 T cell response. The polypeptide was first optimized by taking into account the processing of each peptide at its C-terminal position and the generation of junctional peptides with high affinity for HLA-A*0201. Processing at the C-terminal position was evaluated by using two online predictive models of proteasome cleavage (Netchop: www.cbs.dtu.dk/services/NetChop/, PAProc: www.uni-tuebingen.de/uni/kxi/) (Kesmir et al., 2002; Kuttler et al., 2000; Nussbaum et al., 2001). A peptide was arbitrarily considered to be processed if its cleavage was predicted by both models. The affinity of the new junctional peptides was evaluated by using the Bimas predictive model (Parker et al., 1994). Six polypeptide variants, designated Poly-1 to Poly-6, encompassed all possible peptide arrangements (Table 4). None of the six variants was associated with cleavage of all three peptides in the predictive models (Table 5). Moreover, Poly-1, Poly-3, Poly-4 and Poly-5 generated junctional peptides with high predictive scores for binding to HLA-A*0201 (Table 4). One of these peptides (YLYLQVNSL (SEQ ID NO: 11); Poly-1 and -3) matched a self peptide derived from the variable heavy chain region of human immunoglobulin.

TABLE 4

In silico analysis of the six possible polypeptide variants: generation of junctional peptides predicted to have high HLA-A*0201 affinity

| Polypeptide | | Sequence | Sequence of junctional epitope | Bimas Score |
|---|---|---|---|---|
| Poly-1 | M-N-T | YLEYRQVPV-YLEEITGYL-YLQVNSLQTV (SEQ ID No: 3) | YLYLQVNSL (SEQ ID No: 11) | 723.245 |
| Poly-2 | M-T-N | YLEYRQVPV-YLQVNSLQTV-YLEEITGYL (SEQ ID No: 4) | | |
| Poly-3 | N-T-M | YLEEITGYL-YLQVNSLQTV-YLEYRQVPV (SEQ ID No: 5) | YLYLQVNSLQ (SEQ ID No: 12) | 723.245 |
| Poly-4 | N-M-T | YLEEITGYL-YLEYRQVPV-YLQVNSLQTV (SEQ ID No: 6) | YLYLEYRQV (SEQ ID No: 13) | 307.142 |
| Poly-5 | T-N-M | YLQVNSLQTV-YLEEITGYL-YLEYRQVPV (SEQ ID No: 7) | YLYLEYRQV (SEQ ID No: 14) | 307.142 |
| Poly-6 | T-M-N | YLQVNSLQTV-YLEYRQVPV-YLEEITGYL (SEQ ID No: 2) | | |

TABLE 5

In silico analysis of the six possible polypeptide variants: prediction of proteasome cleavage positions in the six possible polypeptide configurations.

| | Cleavage prediction algorithm | Sequence and site of cleavage (\| and (\|)) | SEQ ID NO. | Number of predicted processed peptides[c] |
|---|---|---|---|---|
| Poly-1 | Paproc[a] | YLEYRQV\|PVY\|L\|E\|EITGY\|L\|Y(\|)L\|QV\|NSLQTV | SEQ ID NO:3 | 0 |
| | Netchopp[b] | Y\|L\|EY\|RQVPVY\|L\|EEITGY\|L\|Y\|L\|QVNSL\|QTV | SEQ ID NO:3 | 0 |
| Poly-2 | Paproc | YLEYRQV\|PVY\|L\|QV\|N(\|)SLQT\|VYLE\|EITGYL | SEQ ID NO:4 | 0 |
| | Netchopp | Y\|L\|EY\|RQVPVY\|L\|QV\|NSL\|QT\|V\|Y\|LEEITGYL | SEQ ID NO:4 | 0 |
| Poly-3 | Paproc | YLEEITGY\|L\|Y(\|)L\|QV\|NSLQT\|VYLE\|Y(\|)RQVPV | SEQ ID NO:5 | 0 |
| | Netchopp | YLEEITGY\|L\|Y\|L\|QVNSL\|QTV\|Y\|L\|EY\|RQVPV | SEQ ID NO:5 | 0 |
| Poly-4 | Paproc | YLEEITGY\|L\|YL\|EYRQV\|PVY\|L\|QV\|N(\|)SLQTV | SEQ ID NO:6 | 0 |
| | Netchopp | YLEEITGY\|L\|Y\|L\|EYRQVPVY\|L\|QV\|NSL\|QTV | SEQ ID NO:6 | 0 |
| Poly-5 | Paproc | YLQVNSLQT\|VYLE\|EITGY\|L\|YL\|EYRQVPV | SEQ ID NO:7 | 0 |
| | Netchopp | Y\|L\|QV\|NSL\|QTV\|Y\|L\|EEITGY\|L\|Y\|L\|EYRQVPV | SEQ ID NO:7 | 0 |
| Poly-6 | Paproc | YLQVNSLQT\|VYLE\|Y(\|)RQV\|PVY\|L\|E\|EITGYL | SEQ ID NO:2 | 0 |
| | Netchopp | Y\|L\|QV\|NSL\|QTV\|Y\|L\|EY\|RQVPVY\|L\|EEITGYL | SEQ ID NO:2 | 0 |

[a] For Paproc, (\|) symbolizes a low probability of cleavage.
[b] For Netchopp, the threshold was set at 0.5 and the network used was: "C-term 1.0. C-term 2.0 and 20S".
[c] Cleavage prediction by both models was required to consider that a peptide would be processed As this predictive approach failed to identify the polypeptide variant with the highest theoretical efficiency, the variants were experimentally tested for their capacity to generate a trispecific CD8 T cell response in vivo (HHD mice) and in vitro (healthy HLA-A*0201 donor).

HHD mice were vaccinated with each polypeptide, and CD8 T cells specific for the individual peptides were identified in draining lymph nodes by using specific tetramers. All six polypeptide variants were immunogenic in HHD mice (i.e., they generated a response to at least one peptide) but the frequency of responding mice varied from one variant to the other. The most immunogenic variants were Poly-1, Poly-3 and Poly-6, with 100%, 87% and 83% of responding mice, respectively (Table 6). Poly-2, Poly-4 and Poly-5 induced a response in respectively 57%, 62% and 62% of vaccinated mice. The frequency of strong responses (% of tetramer-positive CD8 cells at least twice the cutoff value; designated ++) was highest with Poly-6 (41% of all responses), Poly-3 (30% of all responses) and Poly-1 (25% of all responses). The responses were directed against MAGE-A$_{248V9}$ in 74% of responding mice, HER-2/neu$_{402Y}$ in 71% and TERT$_{988Y}$ in 55%. Analysis of the immune responses in individual mice showed that Poly-6 induced a trispecific response in 67% of vaccinated mice, followed by Poly-4 (37.5%), Poly-1 (28.5%), Poly-5 (25%) and Poly-3 (12.5%). Poly-2 did not induce a trispecific response in any mice.

TABLE 6

CD8 T cell response against MAGE-A$_{248V9}$, HER-2/neu$_{402Y}$ and TERT$_{988Y}$ in individual mice immunized with the different polypeptides.

| | Specific T CD8 response against | | |
|---|---|---|---|
| | MAGE-A$_{248V9}$ | HER-2/neu$_{402Y}$ | TERT$_{988Y}$ |
| Poly-1 | + | ++ | + |
| | - | + | - |
| | + | ++ | + |
| | - | + | - |
| | + | + | - |
| | + | - | - |
| | ++ | - | - |
| Poly-2 | - | + | + |
| | - | ++ | + |
| | - | + | - |
| | - | - | - |
| | - | - | - |
| | - | - | - |
| | + | - | - |

TABLE 6-continued

| Polypeptide | | | |
|---|---|---|---|
| Poly-3 | + | + | − |
| | − | + | − |
| | ++ | ++ | ++ |
| | ++ | − | − |
| | + | − | − |
| | + | − | − |
| | + | − | − |
| | − | − | − |
| Poly-4 | − | − | + |
| | ++ | ++ | ++ |
| | − | − | + |
| | − | − | − |
| | ++ | ++ | ++ |
| | − | − | − |
| | ++ | ++ | ++ |
| | − | − | − |
| Poly-5 | − | + | − |
| | − | − | − |
| | ++ | ++ | ++ |
| | ++ | ++ | ++ |
| | + | + | − |
| | − | − | − |
| | − | − | − |
| | + | − | − |
| Poly-6 | + | ++ | + |
| | + | + | + |
| | + | ++ | + |
| | + | − | + |
| | + | ++ | + |
| | − | − | − |
| | − | − | − |
| | ++ | ++ | ++ |
| | − | + | − |
| | ++ | ++ | ++ |
| | ++ | ++ | ++ |
| | ++ | ++ | ++ |

The immune response was evaluated by measuring the % of tetramer-positive CD8 T cells in the draining lymph nodes of vaccinated mice.
"−": percentage of tetramer positive CD8 T cells below the cutoff, as defined in Materials and Method (0.16% for MAGE-A$_{248V9}$, 0.13% for HER-2/neu$_{402Y}$, and 0.16% for TERT$_{988Y}$).
"+": percentage one to two-fold the cutoff.
"++": percentage more than twice the cutoff.
The shaded lines correspond to mice responding to all three peptides.

These results were confirmed with human cells in vitro. Each polypeptide (except for Poly-2, which was very weakly immunogenic in HHD mice) was tested with cells from two to five healthy donors. In vitro immune responses were assessed by measuring the percentage of CD8 cells producing IFNγ after specific peptide activation. All five polypeptides stimulated T cells to respond to at least one peptide in 80% to 100% of donors. However, only Poly-6 and Poly-1 induced trispecific CTL responses. Poly-6 induced responses to all three peptides in 80% of donors, compared to only 25% of donors with Poly-1 (Table 7). Poly-6 also elicited the strongest responses (against MAGE-A$_{248V9}$ in donors #D7017 and #D7225; and against HER-2/neu$_{402Y}$ in donor #D7744)

TABLE 7

Peptide-specific CD8 T cells induced by polypeptide stimulation of healthy human donor PBMC.

| | | Specific T CD8 response against | | |
|---|---|---|---|---|
| Polypepide | Donor | MAGE-A$_{248V9}$ | HER-2/neu$_{402Y}$ | TERT$_{988Y}$ |
| Poly-1 | D9442 | ++ | ++ | − |
| | D0204 | ++ | + | − |
| | D7131 | + | ++ | + |
| | D1100 | − | − | + |
| Poly-3 | D9242 | ++ | + | − |
| | D3031 | − | + | − |
| Poly-4 | D3031 | − | − | + |
| | D9242 | − | − | + |
| | D7131 | + | − | + |

TABLE 7-continued

| | | | | |
|---|---|---|---|---|
| Poly-5 | D7771 | − | + | + |
| | D0204 | + | + | − |
| | D7017 | + | − | + |
| Poly-6 | D7744 | + | +++ | + |
| | D4212 | + | + | + |
| | D7017 | +++ | + | + |
| | D7225 | +++ | + | + |
| | D7601 | − | − | − |

Peptide-specific CD8 T cells were generated by in vitro stimulation of PBMC from healthy donors with the different polypeptides. The specificity of induced CD8 T cells was evaluated by measuring the % of IFNγ-producing CD8 cells after stimulation with peptide-loaded T2 cells as described in Materials and Methods.
"−": % of IFNγ-positive cells less than 2-fold the negative control (irrelevant peptide).
"+" % of IFNγ-positive CD8 cells 2-fold higher than the negative control.
"++" % of IFNγ-positive CD8 cells 2 to 10-fold higher than the negative control.
"+++" % of IFNγ-positive CD8 cells more than ten-fold higher than the negative control.
The shaded lines correspond to donor cells responding to all three peptides.

Together, these results showed that Poly-6 induced frequent and strong trispecific CD8 T cell responses both in vivo (HHD mice) and in vitro (human PBMC).

Discussion

This study of polypeptides composed of three HLA-A*0201-restricted optimized cryptic peptides derived from the universal tumor antigens hTERT, HER-2/neu and MAGE-A identified a polypeptide, named Poly-6 (SEQ ID No: 2), that induced a CTL response against all three component peptides both in HLA-A*0201-expressing transgenic HHD mice and in healthy human donor cells.

There is broad agreement on the influence of polypeptide organization (peptide arrangement, addition of spacers), which should ideally permit appropriate cleavage of all the component peptides and avoid the creation of new junctional peptides with high affinity for the relevant HLA molecule. Several studies have shown that the presence of spacers between peptides increases vaccine efficiency by promoting the cleavage of individual peptides (Livingston et al., 2002; Velders et al., 2001; Wang et al., 2004). Moreover, Ishioka et al. found that the position of a peptide within a polypeptide can affect its immunogenicity. This highlights the importance of the global configuration of the polyepitope (Ishioka et al., 1999). The present results support these findings, as one of the six polypeptide arrangements that were tested was highly immunogenic, while another was minimally effective. This is the first direct demonstration that polypeptide organization must be optimized in order to obtain maximal immunogenicity. These results also show that this optimal organization cannot be foreseen by using current predictive models of proteasome cleavage. Indeed, none of the six candidate polypeptides was predicted to be more efficiently cleaved than the others. Moreover, Poly-2, which failed to elicit a polyspecific response, did not generate junctional peptides predicted to have high affinity for HLA-A*0201 in the Bimas model system.

The inventors also found that vaccination with a mixture of the three peptides was far less efficient than polypeptide vaccination at eliciting a polyspecific response. Interestingly, cells from human donor D7225 responded to all three peptides after stimulation with Poly-6 ex vivo, but only to HER-2/neu$_{402Y}$ after stimulation with the peptide mixture. The use of exogenous peptides has the drawback that the number of peptide/MHC I complexes decays with the same kinetics as the exogenous peptide concentration (Wang et al., 2004). The short half-life of these complexes would lead to a marked loss of priming efficiency (Gett et al., 2003). In contrast, cross-presentation of long peptides by APC could ensure an endogenous source of peptides with slower and more sustained kinetics. This long-peptide strategy has been shown to be more immunogenic than the use of the corresponding short peptides (Zwaveling et al., 2002).

As demonstrated above, the Poly-6 polypeptide of SEQ ID No: 2, which is composed of three optimized cryptic tumor peptides derived from universal tumor antigens (HER-2/neu$_{402Y}$, TERT$_{988Y}$ and MAGE-1A$_{248V9}$), induces a polyspecific response in HLA-A*0201-expressing HHD mice and in human cells ex vivo. This polypeptide has the potential for broad-spectrum tumor vaccination of cancer patients.

REFERENCES

Anderson, K., Cresswell, P., Gammon, M., Hermes, J., Williamson, A. and Zweerink, H. (1991) Endogenously synthesized peptide with an endoplasmic reticulum signal sequence sensitizes antigen processing mutant cells to class I-restricted cell-mediated lysis. *J Exp Med*, 174, 489-492.

Babon, A., Almunia, C., Boccaccio, C., Beaumelle, B., Gelb, M. H., Menez, A., Maillere, B., Abastado, J. P., Salcedo, M. and Gillet, D. (2005) Cross-presentation of a CMV pp 65 epitope by human dendritic cells using bee venom PLA2 as a membrane-binding vector. *FEBS Lett*, 579, 1658-1664.

Brasseur, F., Rimoldi, D., Lienard, D., Lethe, B., Carrel, S., Arienti, F., Suter, L., Vanwijck, R., Bourlond, A., Humblet, Y. and et al. (1995) Expression of MAGE genes in primary and metastatic cutaneous melanoma. *Int J Cancer*, 63, 375-380.

Bungener, L., Idema, J., ter Veer, W., Huckriede, A., Daemen, T. and Wilschut, J. (2002) Virosomes in vaccine development: induction of cytotoxic T lymphocyte activity with virosome-encapsulated protein antigens. *J Liposome Res*, 12, 155-163.

Cibotti, R., Kanellopoulos, J. M., Cabaniols, J. P., Halle-Panenko, O., Kosmatopoulos, K., Sercarz, E. and Kourilsky, P. (1992) Tolerance to a self-protein involves its immunodominant but does not involve its subdominant determinants. *Proc Natl Acad Sci USA*, 89, 416-420.

Doling, A. M., Ballard, J. D., Shen, H., Krishna, K. M., Ahmed, R., Collier, R. J. and Stambach, M. N. (1999) Cytotoxic T-lymphocyte epitopes fused to anthrax toxin induce protective antiviral immunity. *Infect Immun*, 67, 3290-3296.

Fayolle, C., Ladant, D., Karimova, G., Ullmann, A. and Leclerc, C. (1999) Therapy of murine tumors with recombinant Bordetella pertussis adenylate cyclase carrying a cytotoxic T cell epitope. *J Immunol,* 162, 4157-4162.

Firat, H., Zennou, V., Garcia-Pons, F., Ginhoux, F., Cochet, M., Danos, O., Lemonnier, F. A., Langlade-Demoyen, P. and Charneau, P. (2002) Use of a lentiviral flap vector for induction of CTL immunity against melanoma. Perspectives for immunotherapy. *J Gene Med,* 4, 38-45.

Gett, A. V., Sallusto, F., Lanzavecchia, A. and Geginat, J. (2003) T cell fitness determined by signal strength. *Nat Immunol,* 4, 355-360.

Graff-Dubois, S., Faure, O., Gross, D. A., Alves, P., Scardino, A., Chouaib, S., Lemonnier, F. A. and Kosmatopoulos, K. (2002) Generation of CTL recognizing an HLA-A*0201-restricted epitope shared by MAGE-A1, -A2, -A3, -A4, -A6, -A10, and -A12 tumor antigens: implication in a broad-spectrum tumor immunotherapy. *J Immunol,* 169, 575-580.

Gross, D. A., Graff-Dubois, S., Opolon, P., Cornet, S., Alves, P., Bennaceur-Griscelli, A., Faure, O., Guillaume, P., Firat, H., Chouaib, S., Lemonnier, F. A., Davoust, J., Miconnet, I., Vonderheide, R. H. and Kosmatopoulos, K. (2004) High vaccination efficiency of low-affinity epitopes in antitumor immunotherapy. *J Clin Invest,* 113, 425-433.

Haicheur, N., Bismuth, E., Bosset, S., Adotevi, O., Warnier, G., Lacabanne, V., Regnault, A., Desaymard, C., Amigorena, S., Ricciardi-Castagnoli, P., Goud, B., Fridman, W. H., Johannes, L. and Tartour, E. (2000) The B subunit of Shiga toxin fused to a tumor antigen elicits CTL and targets dendritic cells to allow MHC class I-restricted presentation of peptides derived from exogenous antigens. *J Immunol,* 165, 3301-3308.

Ishioka, G. Y., Fikes, J., Hermanson, G., Livingston, B., Crimi, C., Qin, M., del Guercio, M. F., Oseroff, C., Dahlberg, C., Alexander, J., Chesnut, R. W. and Sette, A. (1999) Utilization of MHC class I transgenic mice for development of minigene DNA vaccines encoding multiple HLA-restricted CTL epitopes. *J Immunol,* 162, 3915-3925.

Kesmir, C., Nussbaum, A. K., Schild, H., Detours, V. and Brunak, S. (2002) Prediction of proteasome cleavage motifs by neural networks. *Protein Eng,* 15, 287-296.

Kuttler, C., Nussbaum, A. K., Dick, T. P., Rammensee, H. G., Schild, H. and Hadeler, K. P. (2000) An algorithm for the prediction of proteasomal cleavages. *J Mol Biol,* 298, 417-429.

Lehmann, F., Marchand, M., Hainaut, P., Pouillart, P., Sastre, X., Ikeda, H., Boon, T. and Coulie, P. G. (1995) Differences in the antigens recognized by cytolytic T cells on two successive metastases of a melanoma patient are consistent with immune selection. *Eur J Immunol,* 25, 340-347.

Livingston, B., Crimi, C., Newman, M., Higashimoto, Y., Appella, E., Sidney, J. and Sette, A. (2002) A rational strategy to design multiepitope immunogens based on multiple Th lymphocyte epitopes. *J Immunol,* 168, 5499-5506.

Meseda, C. A., Garcia, A. D., Kumar, A., Mayer, A. E., Manischewitz, J., King, L. R., Golding, H., Merchlinsky, M. and Weir, J. P. (2005) Enhanced immunogenicity and protective effect conferred by vaccination with combinations of modified vaccinia virus Ankara and licensed smallpox vaccine Dryvax in a mouse model. *Virology,* 339, 164-175.

Miconnet, I., Koenig, S., Speiser, D., Krieg, A., Guillaume, P., Cerottini, J. C. and Romero, P. (2002) CpG are efficient adjuvants for specific CTL induction against tumor antigen-derived peptide. *J Immunol,* 168, 1212-1218.

Minev, B., Hipp, J., Firat, H., Schmidt, J. D., Langlade-Demoyen, P. and Zanetti, M. (2000) Cytotoxic T cell immunity against telomerase reverse transcriptase in humans. *Proc Natl Acad Sci USA,* 97, 4796-4801.

Nanda, N. K. and Sercarz, E. E. (1995) Induction of anti-self-immunity to cure cancer. *Cell,* 82, 13-17.

Nussbaum, A. K., Kuttler, C., Hadeler, K. P., Rammensee, H. G. and Schild, H. (2001) PAProC: a prediction algorithm for proteasomal cleavages available on the WWW. *Immunogenetics,* 53, 87-94.

Ofuji, S., Ikeda, M., Tsujitani, S., Ikeguchi, M., Kaibara, N., Yuasa, I., Mitsuya, K., Katoh, M. and Ito, H. (1998) Expression of MAGE-1, MAGE-2 and MAGE-3 genes in human gastric carcinomas; lack of evidence for cytotoxic effects in cases with simultaneous expression of MAGE-3 and HLA-A2. *Anticancer Res,* 18, 3639-3644.

Ogata, S., Uehara, H., Chen, A. and Itzkowitz, S. H. (1992) Mucin gene expression in colonic tissues and cell lines. *Cancer Res,* 52, 5971-5978.

Oukka, M., Manuguerra, J. C., Livaditis, N., Tourdot, S., Riche, N., Vergnon, I., Cordopatis, P. and Kosmatopoulos, K. (1996) Protection against lethal viral infection by vaccination with nonimmunodominant peptides. *J Immunol,* 157, 3039-3045.

Parker, K. C., Bednarek, M. A. and Coligan, J. E. (1994) Scheme for ranking potential HLA-A2 binding peptides based on independent binding of individual peptide sidechains. *J Immunol,* 152, 163-175.

Pascolo, S., Bervas, N., Ure, J. M., Smith, A. G., Lemonnier, F. A. and Perarnau, B. (1997) HLA-A2.1-restricted education and cytolytic activity of CD8(+) T lymphocytes from beta2 microglobulin (beta2m) HLA-A2.1 monochain transgenic H-2 Db beta2m double knockout mice. *J Exp Med,* 185, 2043-2051.

Reese, D. M. and Slamon, D. J. (1997) HER-2/neu signal transduction in human breast and ovarian cancer. *Stem Cells,* 15, 1-8.

Restifo, N. P. (2001) Hierarchy, Tolerance, and Dominance in the Antitumor T-Cell Response. *J Immunother,* 24, 193-194.

Rosenberg, S. A., Yang, J. C. and Restifo, N. P. (2004) Cancer immunotherapy: moving beyond current vaccines. *Nat Med,* 10, 909-915.

Scardino, A., Gross, D. A., Alves, P., Schultze, J. L., Graff-Dubois, S., Faure, O., Tourdot, S., Chouaib, S., Nadler, L. M., Lemonnier, F. A., Vonderheide, R. H., Cardoso, A. A. and Kosmatopoulos, K. (2002) HER-2/neu and hTERT cryptic epitopes as novel targets for broad spectrum tumor immunotherapy. *J Immunol,* 168, 5900-5906.

Slamon, D. J., Clark, G. M., Wong, S. G., Levin, W. J., Ullrich, A. and McGuire, W. L. (1987) Human breast cancer: correlation of relapse and survival with amplification of the HER-2/neu oncogene. *Science,* 235, 177-182.

Tourdot, S., Oukka, M., Manuguerra, J. C., Magafa, V., Vergnon, I., Riche, N., Bruley-Rosset, M., Cordopatis, P. and Kosmatopoulos, K. (1997) Chimeric peptides: a new approach to enhancing the immunogenicity of peptides with low MHC class I affinity: application in antiviral vaccination. *J Immunol,* 159, 2391-2398.

Tourdot, S., Scardino, A., Saloustrou, E., Gross, D. A., Pascolo, S., Cordopatis, P., Lemonnier, F. A. and Kosmatopoulos, K. (2000) A general strategy to enhance immunogenicity of low-affinity HLA-A2.1-associated peptides: implication in the identification of cryptic tumor epitopes. *Eur J Immunol,* 30, 3411-3421.

Van den Eynde, B. J. and van der Bruggen, P. (1997) T cell defined tumor antigens. *Curr Opin Immunol,* 9, 684-693.

Van Pel, A., van der Bruggen, P., Coulie, P. G., Brichard, V. G., Lethe, B., van den Eynde, B., Uyttenhove, C., Renauld, J.

C. and Boon, T. (1995) Genes coding for tumor antigens recognized by cytolytic T lymphocytes. *Immunol Rev,* 145, 229-250.

Vassaux, G., Nitcheu, J., Jezzard, S. and Lemoine, N. R. (2005) Bacterial gene therapy strategies. *J Pathol,* 208, 290-298.

Velders, M. P., Weijzen, S., Eiben, G. L., Elmishad, A. G., Kloetzel, P. M., Higgins, T., Ciccarelli, R. B., Evans, M., Man, S., Smith, L. and Kast, W. M. (2001) Defined flanking spacers and enhanced proteolysis is essential for eradication of established tumors by an epitope string DNA vaccine. *J Immunol,* 166, 5366-5373.

Vonderheide, R. H., Domchek, S. M., Schultze, J. L., George, D. J., Hoar, K. M., Chen, D. Y., Stephans, K. F., Masutomi, K., Loda, M., Xia, Z., Anderson, K. S., Hahn, W. C. and Nadler, L. M. (2004) Vaccination of cancer patients against telomerase induces functional antitumor CD8+ T lymphocytes. *Clin Cancer Res,* 10, 828-839.

Vonderheide, R. H., Hahn, W. C., Schultze, J. L. and Nadler, L. M. (1999) The telomerase catalytic subunit is a widely expressed tumor-associated antigen recognized by cytotoxic T lymphocytes. *Immunity,* 10, 673-679.

Wang, Q. M., Sun, S. H., Hu, Z. L., Zhou, F. J., Yin, M., Xiao, C. J. and Zhang, J. C. (2004) Epitope DNA vaccines against tuberculosis: spacers and ubiquitin modulates cellular immune responses elicited by epitope DNA vaccine. *Scand J Immunol,* 60, 219-225.

Zwaveling, S., Ferreira Mota, S. C., Nouta, J., Johnson, M., Lipford, G. B., Offring a, R., van der Burg, S. H. and Melief, C. J. (2002) Established human papillomavirus type 16-expressing tumors are effectively eradicated following vaccination with long peptides. *J Immunol,* 169, 350-358.

The invention claimed is:

1. A polypeptide which comprises the sequence YLQVNSLQTVX$_1$X$_2$X$_3$YLEYRQVPVX$_1$X$_2$X$_3$YLEEITGYL (SEQ ID No: 1), wherein the TERT$_{988Y}$ (SEQ ID No: 8), MAGE-A$_{248V9}$ (SEQ ID No: 9), and HER-2/neu$_{402Y}$ (SEQ ID No: 10) epitopes are separated by spacers X$_1$X$_2$X$_3$, in which X$_1$, X$_2$ and X$_3$ are any amino acid or none.

2. The polypeptide according to claim 1, further comprising an endoplasmic reticulum-translocating signal sequence at its N-terminal extremity.

3. The polypeptide according to claim 1, further comprising ubiquitin at its C-terminal extremity.

4. The polypeptide according to claim 1, wherein X$_1$=X$_2$=X$_3$=none.

5. The polypeptide according to claim 1, wherein X$_1$=X$_2$=A and X$_3$=Y.

6. The polypeptide according to claim 1, characterized in that it induces a trispecific CD8+ T cells response against TERT$_{988Y}$, MAGE-A$_{248V9}$, and HER-2/neu$_{402Y}$ in a majority of HHD mice vaccinated with said polypeptide.

7. The polypeptide according to claim 1, characterized in that it induces a trispecific CD8+ T cells response against TERT$_{988Y}$, MAGE-A$_{248V9}$, and HER-2/neu$_{402Y}$ in an in vitro assay with human PBMC from healthy HLA-A*0201 donors.

8. The polypeptide according to claim 7, wherein said trispecific CD8+ T cells response is obtained with PBMC from a majority of healthy HLA-A*0201 donors.

9. A nucleic acid molecule encoding a polypeptide according to claim 1.

10. The nucleic acid molecule according to claim 9, which is an expression vector.

11. An isolated dendritic cell loaded with a polypeptide according to claim 1.

12. A complex comprising a peptide delivery vector and a polypeptide according to claim 1.

13. A complex comprising a gene delivery vector and a nucleic acid molecule according to claim 9.

14. A pharmaceutical composition comprising a polypeptide according to claim 1.

15. An isolated dendritic cell transduced with a nucleic acid molecule according to claim 9.

16. A pharmaceutical composition comprising a nucleic acid molecule according to claim 9.

17. A pharmaceutical composition comprising a dendritic cell according to claim 11.

18. A pharmaceutical composition comprising a complex according to claim 12.

19. A method of cancer vaccination or treatment comprising administering a polypeptide according to claim 1 to a patient in need thereof.

20. A method of cancer vaccination or treatment comprising administering a pharmaceutical composition according to claim 17 to an individual.

21. A method of cancer treatment comprising administering to a patient in need thereof dendritic cells according to claim 11 or claim 15, wherein said cells originate from said patient.

* * * * *

SEQUENCE LISTING

```
<160> NUMBER OF SEQ ID NOS: 14

<210> SEQ ID NO 1
<211> LENGTH: 34
<212> TYPE: PRT
<213> ORGANISM: Artificial
<220> FEATURE:
<223> OTHER INFORMATION: Poly-6 with spacers
<220> FEATURE:
<221> NAME/KEY: misc_feature
<222> LOCATION: (11)..(13)
<223> OTHER INFORMATION: Xaa can be any naturally occurring amino acid
<220> FEATURE:
<221> NAME/KEY: misc_feature
<222> LOCATION: (23)..(25)
<223> OTHER INFORMATION: Xaa can be any naturally occurring amino acid

<400> SEQUENCE: 1

Tyr Leu Gln Val Asn Ser Leu Gln Thr Val Xaa Xaa Xaa Tyr Leu Glu
1               5                   10                  15

Tyr Arg Gln Val Pro Val Xaa Xaa Xaa Tyr Leu Glu Glu Ile Thr Gly
            20                  25                  30

Tyr Leu

<210> SEQ ID NO 2
<211> LENGTH: 28
<212> TYPE: PRT
<213> ORGANISM: Artificial
<220> FEATURE:
<223> OTHER INFORMATION: Poly-6

<400> SEQUENCE: 2

Tyr Leu Gln Val Asn Ser Leu Gln Thr Val Tyr Leu Glu Tyr Arg Gln
1               5                   10                  15

Val Pro Val Tyr Leu Glu Glu Ile Thr Gly Tyr Leu
            20                  25

<210> SEQ ID NO 3
<211> LENGTH: 28
<212> TYPE: PRT
<213> ORGANISM: Artificial
<220> FEATURE:
<223> OTHER INFORMATION: Poly-1

<400> SEQUENCE: 3

Tyr Leu Glu Tyr Arg Gln Val Pro Val Tyr Leu Glu Glu Ile Thr Gly
1               5                   10                  15
```

Tyr Leu Tyr Leu Gln Val Asn Ser Leu Gln Thr Val
            20                  25

<210> SEQ ID NO 4
<211> LENGTH: 28
<212> TYPE: PRT
<213> ORGANISM: Artificial
<220> FEATURE:
<223> OTHER INFORMATION: Poly-2

<400> SEQUENCE: 4

Tyr Leu Glu Tyr Arg Gln Val Pro Val Tyr Leu Gln Val Asn Ser Leu
1               5                   10                  15

Gln Thr Val Tyr Leu Glu Glu Ile Thr Gly Tyr Leu
            20                  25

<210> SEQ ID NO 5
<211> LENGTH: 28
<212> TYPE: PRT
<213> ORGANISM: Artificial
<220> FEATURE:
<223> OTHER INFORMATION: Poly-3

<400> SEQUENCE: 5

Tyr Leu Glu Glu Ile Thr Gly Tyr Leu Tyr Leu Gln Val Asn Ser Leu
1               5                   10                  15

Gln Thr Val Tyr Leu Glu Tyr Arg Gln Val Pro Val
            20                  25

<210> SEQ ID NO 6
<211> LENGTH: 28
<212> TYPE: PRT
<213> ORGANISM: Artificial
<220> FEATURE:
<223> OTHER INFORMATION: Poly-4

<400> SEQUENCE: 6

Tyr Leu Glu Glu Ile Thr Gly Tyr Leu Tyr Leu Glu Tyr Arg Gln Val
1               5                   10                  15

Pro Val Tyr Leu Gln Val Asn Ser Leu Gln Thr Val
            20                  25

<210> SEQ ID NO 7
<211> LENGTH: 28
<212> TYPE: PRT
<213> ORGANISM: Artificial
<220> FEATURE:
<223> OTHER INFORMATION: Poly-5

<400> SEQUENCE: 7

Tyr Leu Gln Val Asn Ser Leu Gln Thr Val Tyr Leu Glu Glu Ile Thr
1               5                   10                  15

Gly Tyr Leu Tyr Leu Glu Tyr Arg Gln Val Pro Val
            20                  25

<210> SEQ ID NO 8
<211> LENGTH: 10
<212> TYPE: PRT
<213> ORGANISM: Artificial
<220> FEATURE:
<223> OTHER INFORMATION: TERT988Y

<400> SEQUENCE: 8

Tyr Leu Gln Val Asn Ser Leu Gln Thr Val
1               5                   10

```
<210> SEQ ID NO 9
<211> LENGTH: 9
<212> TYPE: PRT
<213> ORGANISM: Artificial
<220> FEATURE:
<223> OTHER INFORMATION: MAGE-A248V9

<400> SEQUENCE: 9

Tyr Leu Glu Tyr Arg Gln Val Pro Val
1               5

<210> SEQ ID NO 10
<211> LENGTH: 9
<212> TYPE: PRT
<213> ORGANISM: Artificial
<220> FEATURE:
<223> OTHER INFORMATION: HER-2/neu402Y
<220> FEATURE:
<221> NAME/KEY: misc_feature
<223> OTHER INFORMATION: HER-2/neu402Y

<400> SEQUENCE: 10

Tyr Leu Glu Glu Ile Thr Gly Tyr Leu
1               5

<210> SEQ ID NO 11
<211> LENGTH: 9
<212> TYPE: PRT
<213> ORGANISM: Artificial
<220> FEATURE:
<223> OTHER INFORMATION: junctional epitope

<400> SEQUENCE: 11

Tyr Leu Tyr Leu Gln Val Asn Ser Leu
1               5

<210> SEQ ID NO 12
<211> LENGTH: 10
<212> TYPE: PRT
<213> ORGANISM: Artificial
<220> FEATURE:
<223> OTHER INFORMATION: junctional epitope

<400> SEQUENCE: 12

Tyr Leu Tyr Leu Gln Val Asn Ser Leu Gln
1               5                   10

<210> SEQ ID NO 13
<211> LENGTH: 9
<212> TYPE: PRT
<213> ORGANISM: Artificial
<220> FEATURE:
<223> OTHER INFORMATION: junctional epitope

<400> SEQUENCE: 13

Tyr Leu Tyr Leu Glu Tyr Arg Gln Val
1               5

<210> SEQ ID NO 14
<211> LENGTH: 9
<212> TYPE: PRT
<213> ORGANISM: Artificial
<220> FEATURE:
<223> OTHER INFORMATION: junctional epitope
```

<400> SEQUENCE: 14

Tyr Leu Tyr Leu Glu Tyr Arg Gln Val
1               5